(12) United States Patent
Park et al.

(10) Patent No.: US 9,821,059 B2
(45) Date of Patent: Nov. 21, 2017

(54) COMPOSITION FOR STABILIZING PROTEIN AND PHARMACEUTICAL FORMULATION COMPRISING THE SAME

(71) Applicant: Alteogen Inc., Daejeon (KR)

(72) Inventors: Soon Jae Park, Daejeon (KR); Hye-Shin Chung, Daejeon (KR); Jin Hwan Kim, Daejeon (KR); Minsoo Byun, Daejeon (KR); Ji Hyeon Yeon, Daejeon (KR)

(73) Assignee: ALTEOGEN INC., Daejeon (KR)

( * ) Notice: Subject to any disclaimer, the term of this patent is extended or adjusted under 35 U.S.C. 154(b) by 14 days.

(21) Appl. No.: 14/884,312

(22) Filed: Oct. 15, 2015

(65) Prior Publication Data

US 2016/0114036 A1 Apr. 28, 2016

Related U.S. Application Data

(60) Provisional application No. 62/065,127, filed on Oct. 17, 2014.

(51) Int. Cl.
| | |
|---|---|
| *A61K 39/395* | (2006.01) |
| *C07K 16/24* | (2006.01) |
| *A61K 47/26* | (2006.01) |
| *A61K 47/18* | (2017.01) |
| *A61K 9/00* | (2006.01) |

(52) U.S. Cl.
CPC ...... *A61K 39/39591* (2013.01); *A61K 9/0019* (2013.01); *A61K 47/183* (2013.01); *A61K 47/26* (2013.01); *C07K 16/241* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,821,337 A | 10/1998 | Carter et al. | |
| 5,945,098 A | 8/1999 | Sarno et al. | |
| 7,648,702 B2 | 1/2010 | Gombotz et al. | |
| 9,114,166 B2 * | 8/2015 | Krause | A61K 9/19 |
| 9,168,286 B2 | 10/2015 | Chevrier et al. | |
| 9,474,803 B2 * | 10/2016 | Park | A61K 38/1793 |
| 9,707,293 B2 * | 7/2017 | Manning | A61K 39/39591 |
| 2007/0092940 A1 | 4/2007 | Eigenbrot et al. | |
| 2010/0143368 A1 | 6/2010 | King et al. | |
| 2011/0280891 A1 | 11/2011 | Liu et al. | |
| 2012/0116057 A1 | 5/2012 | Kannan et al. | |
| 2014/0255400 A1 | 9/2014 | Maloney et al. | |
| 2015/0071936 A1 * | 3/2015 | Mendiratta | A61K 39/39591 424/142.1 |

FOREIGN PATENT DOCUMENTS

| | | |
|---|---|---|
| JP | 2005-500304 A | 1/2005 |
| JP | 2005-527503 A | 9/2005 |
| JP | 2007-521315 A | 8/2007 |
| JP | 2011-500757 A | 1/2011 |
| JP | 2012-519706 A | 8/2012 |
| WO | 9426295 A1 | 11/1994 |
| WO | 2003000014 A2 | 1/2003 |
| WO | 2003072060 A2 | 9/2003 |
| WO | 2005012353 A1 | 2/2005 |
| WO | 2009053360 A1 | 4/2009 |
| WO | 2010102241 A1 | 9/2010 |
| WO | 2011141926 A2 | 11/2011 |
| WO | 2012143418 A1 | 10/2012 |
| WO | 2013006454 A1 | 1/2013 |

OTHER PUBLICATIONS

Daugherty AL, Mrsny RJ. Formulation and delivery issues for monoclonal antibody therapeutics. Adv Drug Deliv Rev. Aug. 7, 2006;58(5-6):686-706. Epub May 22, 2006.*
Hirano et al. Correlation between thermal aggregation and stability of lysozyme with salts described by molar surface tension increment: an exceptional propensity of ammonium salts as aggregation suppressor. Protein J. Sep. 2007;26(6):423-33.*
Lowe et al. Aggregation, stability, and formulation of human antibody therapeutics. Adv Protein Chem Struct Biol. 2011;84:41-61.*
Nayar R, Manning MC. High throughput formulation: strategies for rapid development of stable protein products. Pharm Biotechnol. 2002;13:177-98.*
Parkins DA, Lashmar UT. The formulation of biopharmaceutical products. Pharmaceutical Sci Technolo Today. Apr. 2000;3(4):129-137.*
Ammonium sulfate 1 M solution, entry in Sigma-Aldrich catalog [online], [retrieved on Jul. 21, 2017]. Retrieved from the Internet:<URL:http://www.sigmaaldrich.com/catalog/product/sigma/50722?lang=en&region=US#>. Jul. 21, 2017.*
Hamada, H., et al., "Effect of Additives on Protein Aggregation", "Current Pharmaceutical Biotechnology", Jun. 2009, pp. 400-407, vol. 10, No. 4.
Philo, J., et al., "Mechanisms of Protein Aggregation", "Current Pharmaceutical Biotechnology", Jun. 2009, pp. 348-351, vol. 10, No. 4.
Stas, P., et al., "Chapter 16: Immunogenicity Assessment of Antibody Therapeutics", "Current Trends in Monoclonal Antibody Development and Manufacturing Biotechnology: Pharmaceutical Aspects, vol. XI", Editor: Shire, S., et al., 2010, pp. 271-291, Publisher: American Association of Pharmaceutical Sciences.

* cited by examiner

*Primary Examiner* — David Romeo
(74) *Attorney, Agent, or Firm* — Hultquist, PLLC; Steven J. Hultquist

(57) ABSTRACT

The present invention relates to a composition for stabilizing TNFα-binding protein exhibiting physiological activity, and more specifically, to a composition for stabilizing protein including basic amino acid and sugar and/or ammonium salt, a pharmaceutical formulation including the same, and a method for stabilizing TNFα-binding protein. The formulation including basic amino acid; and sugar and/or ammonium salt according to the present invention effectively inhibits aggregation, denaturation and oxidation of TNFα-binding protein used for treating various diseases, for example, an anti-TNF-alpha antibody, such that the protein is capable of being preserved and stored for a long time, which is widely usable and effective in a medical field using TNFα-binding protein, for example, an anti-TNF-alpha antibody.

6 Claims, 12 Drawing Sheets

COMPOSITION FOR STABILIZING PROTEIN AND PHARMACEUTICAL FORMULATION COMPRISING THE SAME

CROSS-REFERENCE TO RELATED APPLICATION

This application claims the benefit under 35 U.S.C. §119 of U.S. Provisional Patent Application No. 62/065,127 filed Oct. 17, 2014. The disclosure of U.S. Provisional Patent Application No. 62/065,127 is hereby incorporated herein by reference in its entirety, for all purposes.

TECHNICAL FIELD

The present invention relates to a composition for stabilizing TNFα-binding protein exhibiting physiological activity, and more specifically, to a composition for stabilizing protein including basic amino acid and sugar and/or ammonium salt, a pharmaceutical formulation including the same, and a method for stabilizing TNFα-binding protein.

BACKGROUND ART

Tumor necrosis factor-alpha (TNF-α or TNF) is cytokine which is a member of acute-phase proteins involved in an inflammatory response. TNF-α is mainly secreted by activated macrophages, and is also secreted in a variety of cells such as helper T cells, NK cells, neurons, and the like.

Immune responses of TNF are causes of various diseases (rheumatoid arthritis, ankylosing spondylitis, inflammatory bowel disease, psoriasis, hidradenitis suppurativa and refractory asthma).

Accordingly, TNF inhibitors are often used to treat diseases caused by TNF.

TNF inhibitor protein pharmaceuticals include infliximab (product: Remicade), adalimumab (product: Humira), certolizumab pegol (product name: Cimzia) as monoclonal antibody proteins, and etanercept (product name; Enbrel) antibody as circulating receptor fusion protein.

Production amount of the antibody protein pharmaceuticals has increased in accordance with the development of recombinant technology, cell culture techniques, and purification techniques. However, the antibody protein requires appropriate formulations thereof due to physical and chemical instability caused by a large molecular weight and a complex structure as compared to general protein pharmaceuticals.

The antibody protein has a problem of forming aggregation which is representative phenomenon generated by physical instability. In fact, factors causing aggregation are variously present in purification, formulation, storage processes of the antibody protein. For example, the aggregation may be caused by at least one of the following factors. In purification, pH, salt type, salt concentration, temperature, contact with air, stirring speed, and the like, that are not optimum conditions, affect the aggregation, and in formulation, protein concentration conditions may affect the aggregation. Further, in changing buffers, passing through the filter, stirring, and the like, may affect the aggregation, and in storing, temperature change, pH change, contact with air, stirring, and the like, may affect the aggregation. Besides, the aggregation may occur even when the formulation including the protein is exposed to light. Because when exposed to light, a photoreactive material is produced and combined with other groups to cause variants. In addition, packing container may also be a cause of aggregation. The reason is because trace amount of metal ions exposed from the packing material to the formulation may promote hydrolysis of amide bonds (Current Pharmaceutical Biotechnology, 2009, 10, 348-351, Hamada, H. et al.).

As described above, the aggregation phenomenon may be caused by various factors including environmental factors such as temperature, pH, buffer type, concentration, ionic strength, excipient type, concentration of protein, the presence or absence of reducing materials, the presence of impurities and the state of a container, or purification methods, and the like. However, the aggregation phenomenon shown in the antibody protein is mainly caused by water solubility decreased when hydrophobic regions of the antibody protein are exposed due to structural change. That is, the hydrophobic regions of the protein molecules are assembled to form massive aggregation, wherein the formed aggregation may progress in an irreversible form due to covalent bonding generated between molecules in the antibody protein (Current Pharmaceutical Biotechnology 10(2009), 348-351, Hamada, H. et al.).

The antibody protein aggregated by the above-described reasons generally has reduced activities or loses activities over time. In addition, when these aggregated proteins are administered to a human body, the protein has antigenicity which is not exhibited in a non-aggregation state, which may induce production of an antibody (anti-drug antibody, ADA). Therefore, it is required to develop a method of reducing the aggregation of protein and stabilized formulation of protein having a reduced level of aggregation (Current Trends in Monoclonal Antibody Development and Manufacturing Biotechnology: Pharmaceutical Aspects Volume XI, 2010, pp 271-291).

Under such technical background, the present inventors found that basic amino acid, sugar and/or ammonium salt is capable of inhibiting aggregation of TNFα binding protein, and increasing stability of the protein so as to be easily preserved and stored for a long period of time, and completed the present invention.

DISCLOSURE

An object of the present invention is to provide a composition capable of inhibiting aggregation, denaturation and oxidation of a TNFα-binding antibody having physiological activity, or a method of inhibiting aggregation, denaturation and oxidation of the TNFα-binding antibody.

In order to achieve the foregoing objects, the present invention provides a composition for stabilizing protein by inhibiting aggregation, denaturation and oxidation of protein, and a pharmaceutical formulation including the same.

The present invention also provides a method of stabilizing protein by adding basic amino acid; and sugar and/or ammonium salt to the protein.

BEST MODE

Figure 1:
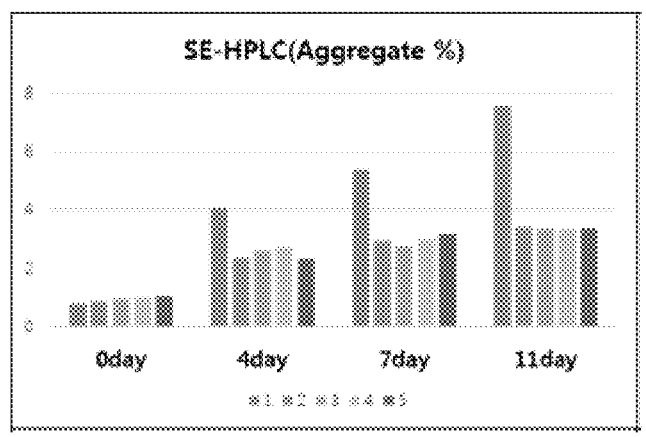
FIG. 1 illustrates results of change in aggregate content (%) for each pH, measured for 11 days at 50° C.

As far as it is not defined in other ways, all technical and scientific terms used in the present specification have the same meaning as being generally appreciated by those skilled in the art to which the present invention pertains. In general, a nomenclature and experimental methods used in the present specification and described below are well known in technical fields and generally used.

In one general aspect, the present invention relates to a composition for stabilizing protein including TNFα-binding protein; basic amino acid; and sugar and/or ammonium salt.

In one exemplary embodiment, the TNFα-binding protein has physiological activity controlling biological functions of TNF-α, such as neutralization of activities of TNF-α, or reduction in binding ability of TNF-α to receptors thereof. In this aspect, the TNFα-binding protein may be, for example, an anti-TNFα antibody or an antigen-binding site thereof, or TNFα receptors or fragments thereof. The binding degree is not specifically limited, but the TNFα-binding protein may have, for example, a dissociation constant (KD) of about $10^{-7}$ to $10^{-13}$ M. The concentration of TNFα-binding protein included in the composition is a concentration exhibiting pharmacological effects, for example, a concentration of 5 to 100 mg/ml, preferably, a concentration of 25 to 75 mg/ml, and more preferably, a concentration of 45 to 55 mg/ml.

In one exemplary embodiment, the basic amino acid may be at least one selected from the group consisting of arginine, histidine, and lysine. The basic amino acid may have a concentration of 5 to 500 mM, preferably, 50 to 500 mM, and more preferably, 50 to 150 mM. In the Examples of the present invention, the basic amino acid having a concentration of 50 to 200 mM was used, and it was confirmed that aggregation of target protein was inhibited in the composition including the basic amino acid having the above-described range.

The composition for stabilizing protein according to the present invention further includes sugar and/or ammonium salt to reduce aggregation, denaturation and oxidation of protein further.

In one exemplary embodiment, the sugar may be at least one selected from the group consisting of mannitol, sucrose, maltose, and trehalose. Here, the sugar may have a concentration of 0.5 to 10% (w/v), preferably, 0.5 to 5% (w/v), and more preferably, 1 to 2.5% (w/v). It was confirmed that aggregation of target protein was inhibited, acidic variants were reduced, and reduction in K0 and/or K1 was inhibited, in the composition including the sugar having the above-described range.

In another exemplary embodiment, the ammonium salt may be at least one selected from the group consisting of ammonium chloride, ammonium sulfate, ammonium carbonate, and ammonium nitrate. Here, the ammonium salt may have a concentration of 5 to 500 mM, preferably, 30 to 150 mM, and more preferably, 40 to 80 mM. It was confirmed that aggregation of target protein was inhibited, acid variants were reduced, and reduction in K0 and/or K1 was inhibited, in the composition including the ammonium salt having the above-described range.

In one exemplary embodiment, the composition according to the present invention may include both of sugar and ammonium salt. When both of sugar and ammonium salt are included, the sugar may have a concentration of 0.5 to 5% (w/v), preferably, 1 to 2% (w/v), and more preferably, 1 to 2.5% (w/v), and the ammonium salt may have a concentration of 30 to 150 mM, preferably, 40 to 80 mM, and more preferably, 40 to 60 mM. It was confirmed that aggregation of target protein was inhibited, acid variants were reduced, and reduction in K0 and/or K1 was inhibited, in the composition including both of the sugar and the ammonium salt each having the above-described range.

Based on the above-description, the composition according to the present invention may include 5 to 100 mg/ml of TNFα-binding protein; 5 to 200 mM of basic amino acid; and 1 to 100% (w/v) of sugar.

In addition, the composition according to the present invention may include 5 to 100 mg/ml of TNFα-binding protein; 5 to 200 mM of basic amino acid; and 5 to 200 mM of ammonium salt.

Further, the composition according to the present invention may include 5 to 100 mg/ml of TNFα-binding protein; 5 to 200 mM of basic amino acid; 1 to 2% (w/v) of sugar; and 40 to 80 mM of ammonium salt.

In one exemplary embodiment, term "stabilization" used herein means any one of the following (a) to (e):
(a) inhibition of denaturation, deamidation or oxidation of TNFα-binding protein;
(b) inhibition of reduction of K0 variants of C-terminal lysine;
(c) inhibition of production of acidic variants;
(d) inhibition of reduction ratio of TNFα-binding protein monomer (the major peak in HPLC of lysine variants of monoclonal antibody); and
(e) inhibition of aggregation of TNFα-binding protein or inhibition of increase in production of fragments thereof.

When the purified adalimumab was tested in Cation exchange high performance chromatography, the two peaks appeared after the main protein peak. The adalimumab with two lysine amino acids cleaved at the C-terminus of antibody is designated as K0; the antibody with one lysine amino acid cleaved at C-terminus is designated as K1. The antibody with two lysine amino acids intact at C-terminus is designated as K2. The modified adalimumab peaks appeared in front of main peak at cation exchange HPLC is called acidic variants.

In another aspect, the present invention relates to a pharmaceutical formulation including the composition. The pharmaceutical formulation may further include a pharmaceutically acceptable carrier, diluent or excipient.

The pharmaceutically acceptable carrier functions as an adjuvant useful for increasing absorption or dispersion of a binding protein, and includes physiologically acceptable solvents, dispersion media, coating agents, antibacterial agents, antifungal agents, isotonic agents, and absorption delaying agents, and the like. Examples of the pharmaceutically acceptable carrier include at least one selected from the group consisting of water, saline, phosphate buffered saline, dextrose, glycerol, ethanol, and the like, and combinations thereof. In many cases, the composition may contain sugar, polyalcohol (for example: mannitol, sorbitol) or isotonic agents such as sodium chloride. The pharmaceutically acceptable carrier may further contain small amounts of auxiliary materials such as wetting agents, emulsifying agents, preservatives or buffers for increasing lifespan or efficiency of the antibody or antibody portions thereof.

In some cases, the formulation may include at least one additional therapeutic agent for treating harmful disorder of TNF-α activity, for example, therapeutic agents, contrast agents, cytotoxic agents, angiogenesis inhibitors, kinase inhibitors, co-administration molecule blockers, adsorption molecule blockers, anti-cytokine antibodies or functional fragments thereof, methotrexate, cyclosporine, rapamycin, FK506, detectable labels, detectable reporters, TNF-α antagonists, anti-rheumatic agents, muscle relaxants, narcotics, non-steroidal anti-inflammatory drugs (NSAIDs), analgesics, anesthetics, sedatives, local anesthetics, neuromuscular blockers, antimicrobial agents, anti-psoriasis agents, corticosteroids, anabolic steroids, erythropoietin, immunological agents, immunoglobulins, immunosuppressive agents, growth hormones, hormone replacement drugs, radiopharmaceuticals, antidepressants, antipsychotics, stimulants, asthma drugs, beta agonists, inhaled steroids, oral steroids, epinephrine, analogs thereof, cytokines and cytokine antagonists.

In still another aspect, the present invention provides a method of treating diseases including administrating the composition or pharmaceutical formulation. For example, the composition or pharmaceutical formulation may be administered intramuscularly, intravenously, intratumorally, orally, intranasally, pulmonary, or subcutaneously. The composition according to the present invention may be prepared as an injectable solution. The injectable solution may be prepared in a liquid or lyophilized dosage form included in flint or amber vials, ampoules or pre-filled syringe. The composition may have an appropriate pH of 5.7 to 6.3.

In another aspect, the present invention provides a method of stabilizing protein by adding basic amino acid; and sugar and/or ammonium salt to a solution including the TNFα-binding protein.

One Example of the present invention used an antibody protein obtained by expressing antibody protein having the same amino acid sequence as an anti-TNF-alpha antibody used in the commercially available anti-arthritis drug, Humira®, in CHO cells, and purifying the antibody protein to a high purity.

In addition, experiments were performed to determine whether the basic amino acid and sugar according to the present invention effectively inhibit aggregation, denaturation and oxidation of anti-TNF-alpha antibody to be effective for stabilizing the formulation.

However, the present invention is not limited thereto, but the composition according to the present invention may be used to stabilize compositions for treating various diseases according to types of physiologically active proteins and anti-TNF-alpha antibodies usable for treatment. Therefore, the present invention may provide compositions for treating various diseases.

Hereinafter, the present invention will be described in detail with reference to the following Examples. However, the following examples are only for exemplifying the present invention, and it will be obvious to those skilled in the art that the scope of the present invention is not construed to be limited to these examples.

EXAMPLE 1

Figure 2:
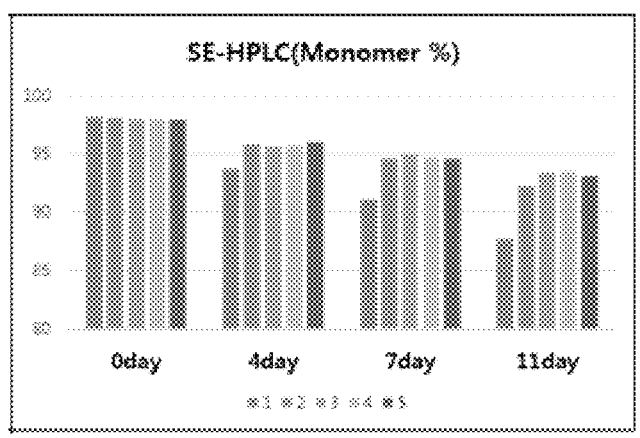
FIG. 2 illustrates results of change in monomer content (%) for each pH, measured for 11 days at 50° C.
Figure 3:
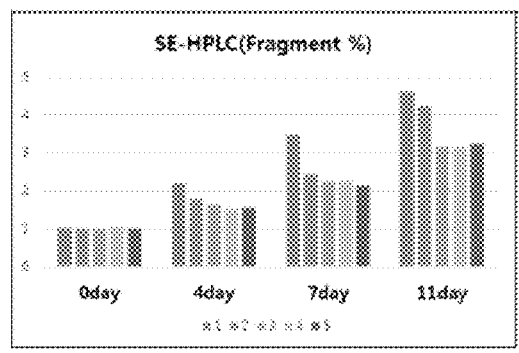
FIG. 3 illustrates results of change in fragment content (%) for each pH, measured for 11 days at 50° C.

The present experiment is to confirm stability for each pH in order to figure out the most stable pH of antibody protein (Adalimumab). As exemplified in Table 1, the stability was confirmed by storing samples prepared for each pH based on citrate-phosphate buffer at 50° C. a and analyzing aggregation, monomer, and fragment contents over time by SE (Size Exclusion)-HPLC. The analysis was performed by TSKgel G3000SWXL (300×7.8 mm) HPLC analysis column while loading 0.2M potassium phosphate, 0.25M potassium chloride, with a pH 6.2 buffer at 0.5 ml/min. From measurement results for 11 days at 50° C., it was confirmed that a reduction rate of monomer was the lowest at pH 5.7 and pH 6.3 as shown in FIG. 2. In addition, it was observed that an increase rate of aggregate and fragment was also low at pH 5.7 and pH 6.3 as shown in FIGS. 1 and 3, and accordingly, the most stable pH of the protein was pH 5.7 and pH 6.3.

Figure 4:
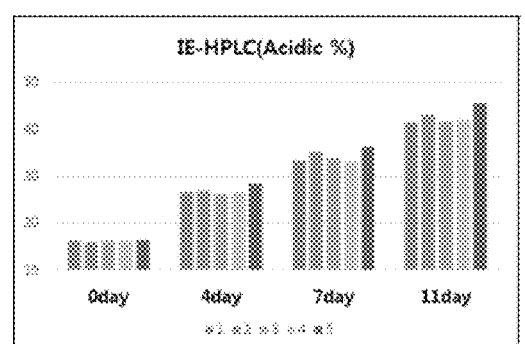
FIG. 4 illustrates results of change in acidic variant content (%) depending on change in charge for each pH, measured for 11 days at 50° C.
Figure 5:
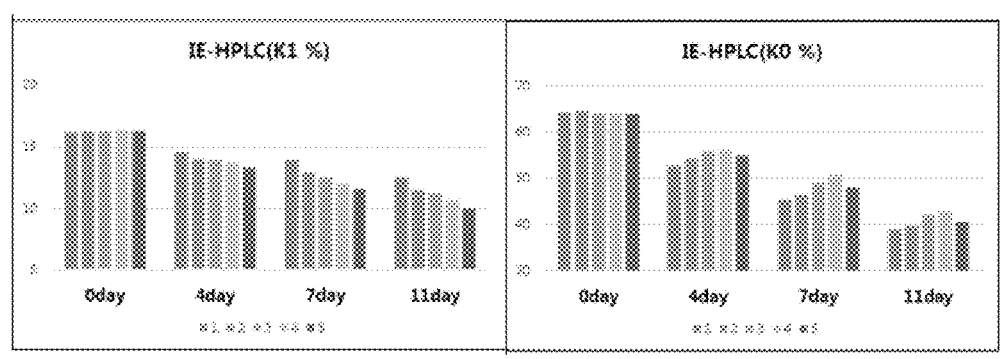
FIG. 5 illustrates results of change in K0 variant content (%) depending on change in charge for each pH, measured for 11 days at 50° C.

Further, charges of the antibody were changed by denaturation, deamidation, oxidation, and the like. It was considered that the K0, K1, and K2 variant peaks were moved to acidic variant peaks by denaturation, deamidation, oxidation, and the like. In order to analyze the above observation, the analysis was performed by ProPac WCX-10(250×4 mm) HPLC analysis column including 50 mM sodium phosphate (pH 7.5) as a base with a sodium chloride concentration gradient. From measurement results for 11 days at 50° C., it was confirmed that a reduction rate of K0 variant was the lowest at pH 5.7 and pH 6.3 as shown in FIG. 5. In addition, as shown in FIG. 4, productions of acidic variants were inhibited at pH 5.7 and pH 6.3.

TABLE 1 sample prepared according to the different pH based on citrate-phosphate buffer

| No. | Protein (mg/ml) | Citrate-phosphate (mM) | pH |
|---|---|---|---|
| 1 | 50 | 21.45 | 4.86 |
| 2 | 50 | 21.45 | 5.25 |
| 3 | 50 | 21.45 | 5.74 |
| 4 | 50 | 21.45 | 6.33 |
| 5 | 50 | 21.45 | 6.61 |

EXAMPLE 2

Figure 6:
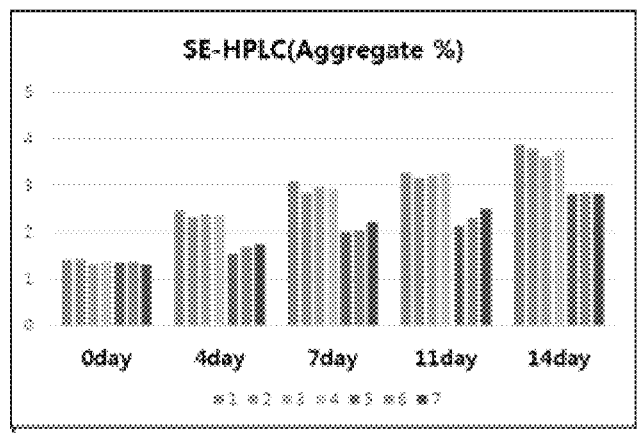
FIG. 6 illustrates results of change in aggregate content (%) for each stabilizer, measured for 14 days at 50° C.
Figure 7:
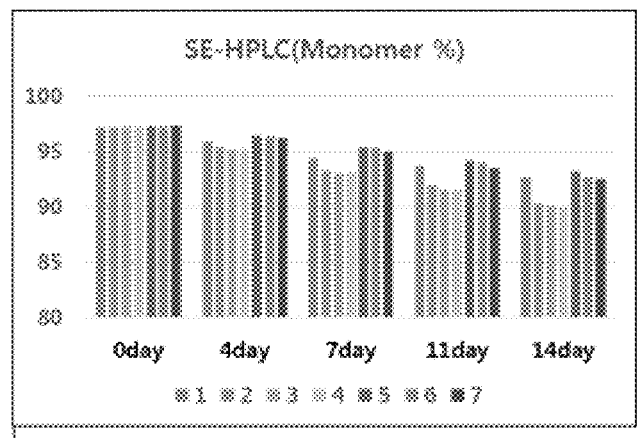
FIG. 7 illustrates results of change in monomer content (%) for each stabilizer, measured for 14 days at 50° C.
Figure 8:
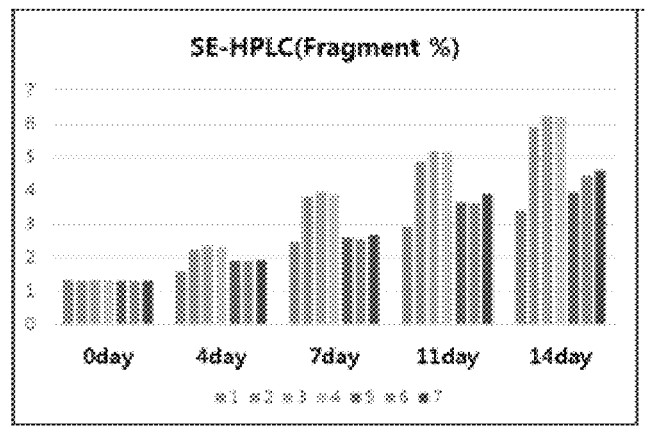
FIG. 8 illustrates results of change in fragment content (%) for each stabilizer, measured for 14 days at 50° C.

The present experiment is to confirm stability for each stabilizer in order to figure out the most stable stabilizer of the protein. As exemplified in Table 2, the stability was confirmed by storing samples prepared for each stabilizer at 50° C. and analyzing aggregation, monomer, and fragment contents over time by SE-HPLC. The analysis was performed by TSK gel G3000SWXL(300×7.8 mm) HPLC analysis column while loading 0.2M potassium phosphate, 0.25M potassium chloride, with a pH 6.2 buffer at 0.5 ml/min. From measurement results for 14 days at 50° C., it was confirmed that as compared to the case of addition of salts, a reduction rate of monomer was low and an increase rate of aggregate and fragment was also low when adding basic amino acid, as shown in FIGS. 6, 7 and 8.

Figure 9:
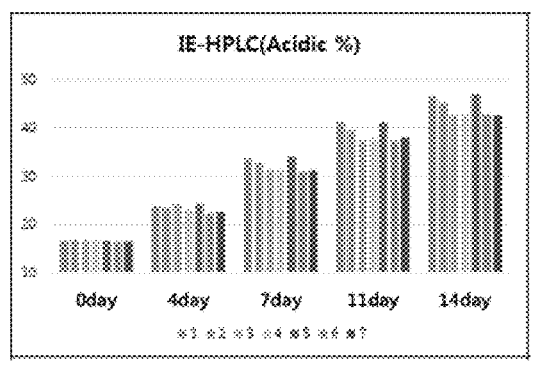
FIG. 9 illustrates results of change in acidic variant contents (%) depending on change in charge for each stabilizer, measured for 14 days at 50° C.
Figure 10:
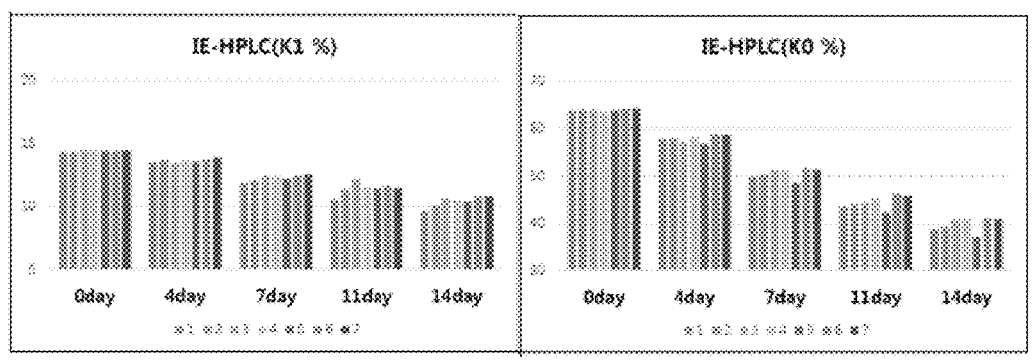
FIG. 10 illustrates results of change in K0 variant contents (%) depending on change in charge for each stabilizer, measured for 14 days at 50° C.

Further, charges of the antibody were changed by denaturation, deamidation, oxidation, and the like. It was considered that the K0, K1, and K2 variant peaks were moved to acidic variant peaks by denaturation, deamidation, oxidation, and the like. In order to analyze the above observation, the analysis was performed by ProPac WCX-10(250×4 mm) HPLC analysis column including 10 mM sodium phosphate (pH 7.5) as a base with a sodium chloride concentration gradient. From measurement results for 14 days at 50° C., it was confirmed that a reduction rate of K0 variant was the lowest in arginine and lysine containing composition as shown in FIG. 10. As shown in FIG. 9, production of acidic variants was inhibited in arginine and lysine.

EXAMPLE 3

The present experiment is to confirm that a novel formulation including arginine or sugar is more stable than the existing commercialized formulation Humira® by comparing the novel formulation with the existing commercialized formulation Humira®.

Figure 11:
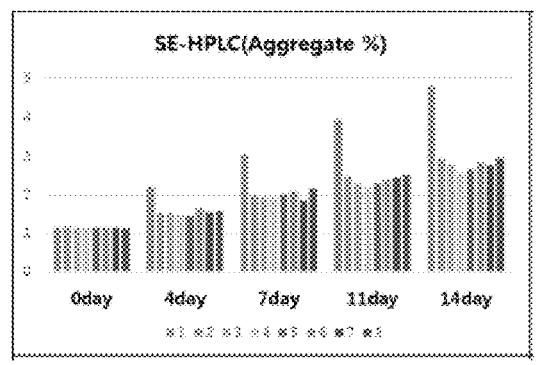
FIG. 11 illustrates results of change in aggregate content (%) for each arginine concentration and each sugar, measured for 14 days at 50° C.
Figure 12:
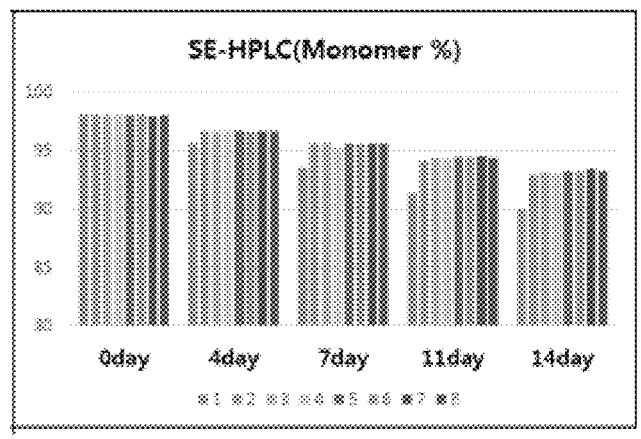
FIG. 12 illustrates results of change in monomer content (%) for each arginine concentration and each sugar, measured for 14 days at 50° C.
Figure 13:
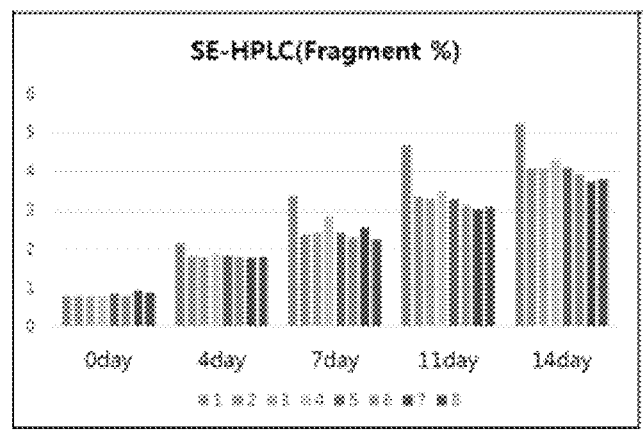
FIG. 13 illustrates results of change in fragment content (%) for each arginine concentration and each sugar, measured for 14 days at 50° C.

The stability was confirmed by storing samples of Table 3, prepared for each sugar and arginine concentration at 50° C. and analyzing aggregation, monomer, and fragment contents over time by SE-HPLC. The analysis was performed by TSKgel G3000SWXL (300×7.8 mm) HPLC analysis column while loading 0.2M potassium phosphate, 0.25M potassium chloride, with a pH 6.2 buffer at 0.5 ml/min. From measurement results for 14 days at 50° C., it was confirmed that as compared to the formulation including only arginine and the Humira® formulation, a reduction rate of a monomer was low and an increase rate of the aggregate and the fragment was also low in the formulation including arginine and/or sugar as shown in FIGS. 11, 12, and 13.

Figure 14:
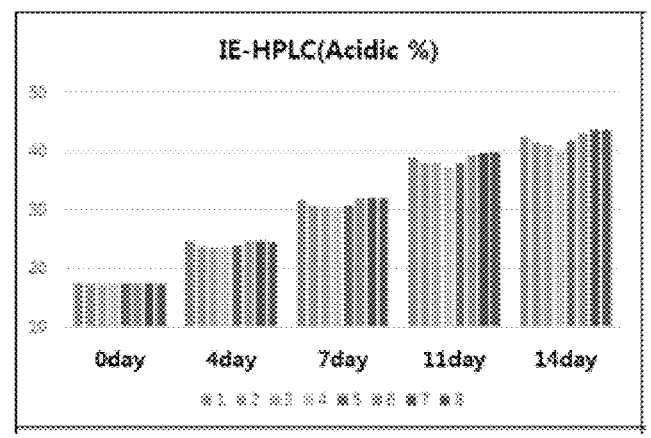
FIG. 14 illustrates results of change in acidic variant contents (%) depending on change in charge for each arginine concentration and each sugar, measured for 14 days at 50° C.
Figure 15:
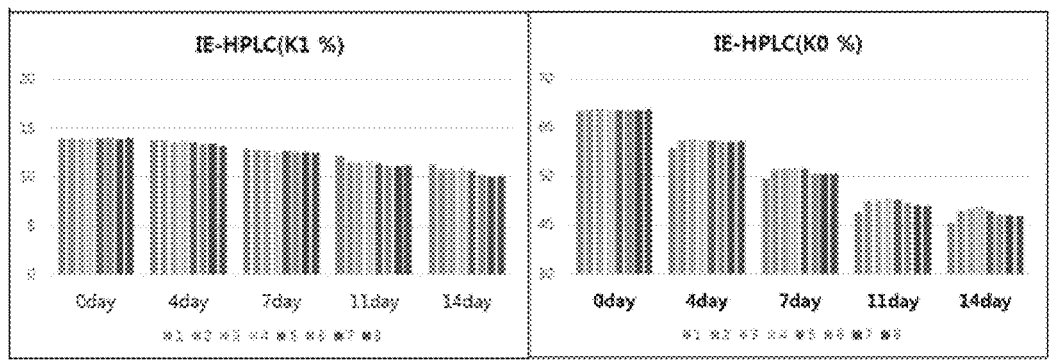
FIG. 15 illustrates results of change in K0 variant contents (%) depending on change in charge for each arginine concentration and each sugar, measured for 14 days at 50° C.

Further, charges of the antibody were changed by denaturation, deamidation, oxidation, and the like. It was considered that in adalimumab, the K0, K1, and K2 variant peaks were moved to acidic variant peaks by denaturation, deamidation, oxidation, and the like. In order to analyze the above observation, the analysis was performed by ProPac WCX-10 (250×4 mm) HPLC analysis column including 10 mM sodium phosphate (pH 7.5) as a base with a sodium chloride concentration gradient. From measurement results for 14 days at 50° C., it was confirmed that a reduction rate of K0 variant was low in the formulation including both of arginine and sugar as compared to the formulation including only arginine and the Humira® formulation as shown in FIG. 15. Further, as shown in FIG. 14, production of acidic variants was inhibited in the formulation including both of arginine and sugar as compared to the formulation including only arginine and Humira® formulation as shown in FIG. 14.

TABLE 2 sample prepared according to the types of stabilizer

| No. | Protein (mg/ml) | Citrate-phosphate (mM) | Salt (mM) | | | Amino acid (mM) | | | pH |
|---|---|---|---|---|---|---|---|---|---|
| | | | NH₄Cl | NaCl | KCl | Histidine | Arginine | Lysine | |
| 1 | 50 | 21.45 | — | — | — | — | — | — | 5.84 |
| 2 | 50 | 21.45 | 50 | — | — | — | — | — | 5.9 |
| 3 | 50 | 21.45 | — | 100 | — | — | — | — | 5.83 |
| 4 | 50 | 21.45 | — | — | 100 | — | — | — | 5.83 |
| 5 | 50 | 21.45 | — | — | — | 100 | — | — | 5.91 |
| 6 | 50 | 21.45 | — | — | — | — | 100 | — | 5.9 |
| 7 | 50 | 21.45 | — | — | — | — | — | 100 | 5.91 |

TABLE 3 sample prepared according to the types of sugar and concentrations of arginine.

| No. | Protein (mg/ml) | Citrate-phosphate (mM) | NCl (mM) | Polysorbate 80 (%) | Arginine (mM) | Trehalose (%) | Mannitol (%) | Sucrose (%) | pH |
|---|---|---|---|---|---|---|---|---|---|
| 1 | 50 | 21.45 | 105 | 0.1 | — | — | 1.2 | — | 5.2 |
| 2 | 50 | 21.45 | — | — | 100 | — | — | — | 5.8 |
| 3 | 50 | 21.45 | — | — | 100 | 1.2 | — | — | |
| 4 | 50 | 21.45 | — | — | 100 | — | 1.2 | — | |
| 5 | 50 | 21.45 | — | — | 100 | — | — | 1.2 | |
| 6 | 50 | 21.45 | — | — | 50 | 1.2 | — | — | |
| 7 | 50 | 21.45 | — | — | 50 | — | 1.2 | — | |
| 8 | 50 | 21.45 | — | — | 50 | — | — | 1.2 | |

EXAMPLE 4

The present experiment is to compare the existing commercialized formulation Humira® and novel formulation including arginine and various isotonic agents, and to confirm that the formulation including arginine and isotonic agents of Table 4 is more stable than the existing commercialized formulation Humira®.

Figure 16:
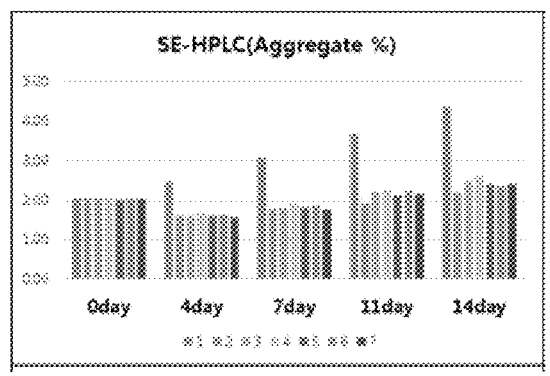
FIG. 16 illustrates results of change in aggregate content (%) for each arginine concentration and each isotonic agent, measured for 14 days at 50° C.
Figure 17:
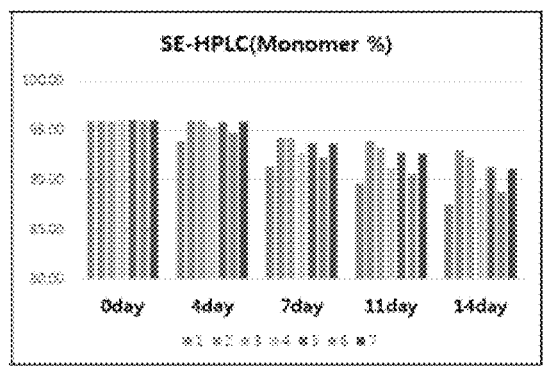
FIG. 17 illustrates results of change in monomer content (%) for each arginine concentration and each isotonic agent, measured for 14 days at 50° C.
Figure 18:
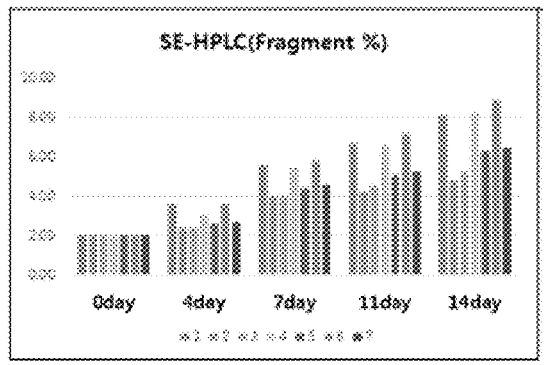
FIG. 18 illustrates results of change in fragment content (%) for each arginine concentration and each isotonic agent, measured for 14 days at 50° C.
Figure 19:
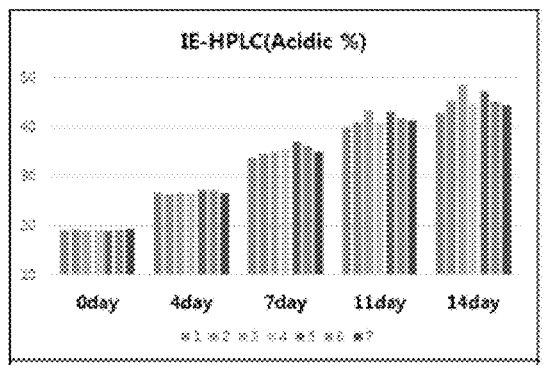
FIG. 19 illustrates results of change in acidic variant contents (%) depending on change in charge for each arginine concentration and each isotonic agent, measured for 14 days at 50° C.

The stability was confirmed by storing samples at 50° C., the sample prepared by adding each isotonic agent to satisfy 300 Osmol/Kg, and analyzing aggregation, monomer, and fragment contents over time by SE-HPLC. The analysis was performed by TSKgel G3000SWXL (300×7.8 mm) HPLC analysis column while loading 0.2M potassium phosphate, 0.25M potassium chloride, with a pH 6.2 buffer at 0.5 ml/min. From measurement results for 14 days at 50° C., it was confirmed that a reduction rate of monomer was low and an increase rate of aggregate and fragment was also low in the formulation including the isotonic agent as compared to the Humira® formulation as shown in FIGS. 16, 17, and 18.

Figure 20:
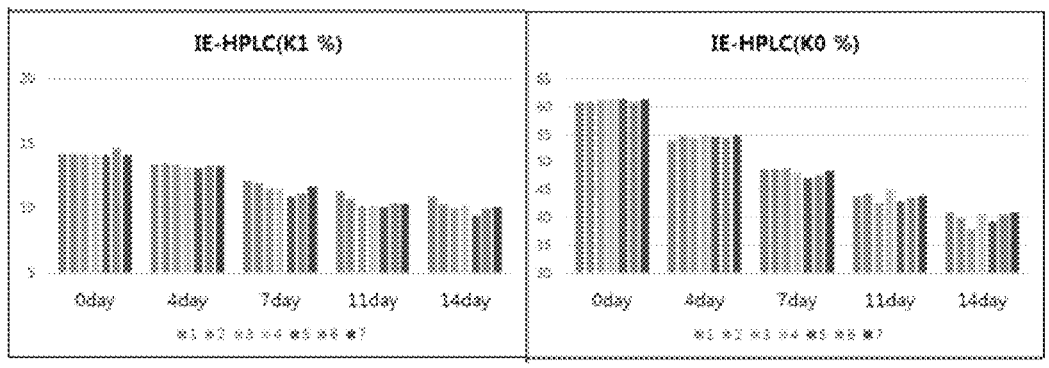
FIG. 20 illustrates results of change in K0 variant contents (%) depending on change in charge for each arginine concentration and each isotonic agent, measured for 14 days at 50° C.

Further, charges of the antibody were changed by denaturation, deamidation, oxidation, and the like. It was considered that in adalimumab, the K0, K1, and K2 variant peaks were moved to acidic variant peaks by denaturation, deamidation, oxidation, and the like. In order to analyze the above observation, the analysis was performed by ProPac WCX-10 (250×4 mm) HPLC analysis column including 50 mM sodium phosphate (pH 7.5) as a base with a sodium chloride concentration gradient. From measurement results for 14 days at 50° C., it was confirmed that a reduction rate of K0 variant in the formulation 2 including arginine and mannitol, and the formulation 7 including arginine and ammonium sulfate was the same as that of the Humira® formulation as shown in FIG. 20.

TABLE 4 formulations comprising Arginie and various types of isotonic agents

| | | | | | 100 mM Arginine | | | | | | |
|---|---|---|---|---|---|---|---|---|---|---|---|
| No. | Protein (mg/ml) | Citrate-phosphate (mM) | NCl (mM) | Polysorbate 80 (%) | Mannitol (%) | Mannitol (%) | Sucrose (%) | NaCl (mM) | Ammonium acetate (mM) | Ammonium chloride (mM) | Ammonium sulfate (mM) | Osmolarity (Osmol/kg) |
| 1 | 50 | 21.45 | 105 | 0.1 | 1.2 | — | — | — | — | — | — | 341 |
| 2 | 50 | 21.45 | — | — | — | 2.75 | — | — | — | — | — | 298 |
| 3 | 50 | 21.45 | — | — | — | — | 5.1 | — | — | — | — | 303 |
| 4 | 50 | 21.45 | — | — | — | — | — | 87.5 | — | — | — | 297 |
| 5 | 50 | 21.45 | — | — | — | — | — | — | 87 | — | — | 298 |
| 6 | 50 | 21.45 | — | — | — | — | — | — | — | 93 | — | 299 |
| 7 | 50 | 21.45 | — | — | — | — | — | — | — | — | 77.5 | 299 |

EXAMPLE 5

Formulations were prepared by varying types of acids, which adjust pH of the composition, and the stability was confirmed.

TABLE 5

Formulations according to types of acids adjusting pH

| | | | | | | 100 mM Arginine | | | | | |
|---|---|---|---|---|---|---|---|---|---|---|---|
| No. | Protein (mg/ml) | Citrate-phosphate (mM) | NCl (mM) | Polysorbate 80 (%) | Mannitol (%) | HCl | 0.5M Citric acid | Phosphoric acid | 0.5M Succinic acid | Acetic acid | pH |
| 1 | 50 | 21.45 | 105 | 0.1 | 1.2 | — | — | — | — | — | 5.2 |
| 2 | 50 | 21.45 | — | — | — | 0 | — | — | — | — | 5.9 |
| 3 | 50 | 21.45 | — | — | — | — | 0 | — | — | — | |
| 4 | 50 | 21.45 | — | — | — | — | — | 0 | — | — | |

TABLE 5-continued

Formulations according to types of acids adjusting pH

|  |  |  |  |  | 100 mM Arginine | | | | |
|---|---|---|---|---|---|---|---|---|---|
| No. | Protein (mg/ml) | Citrate-phosphate (mM) | NCl (mM) | Polysorbate 80 (%) | Mannitol (%) | HCl | 0.5M Citric acid | 0.5M Phosphoric acid | 0.5M Succinic acid | Acetic acid | pH |
| 5 | 50 | 21.45 | — | — | — | — | — | — | 0 | — | |
| 6 | 50 | 21.45 | — | — | — | — | — | — | — | 0 | |

Figure 21:
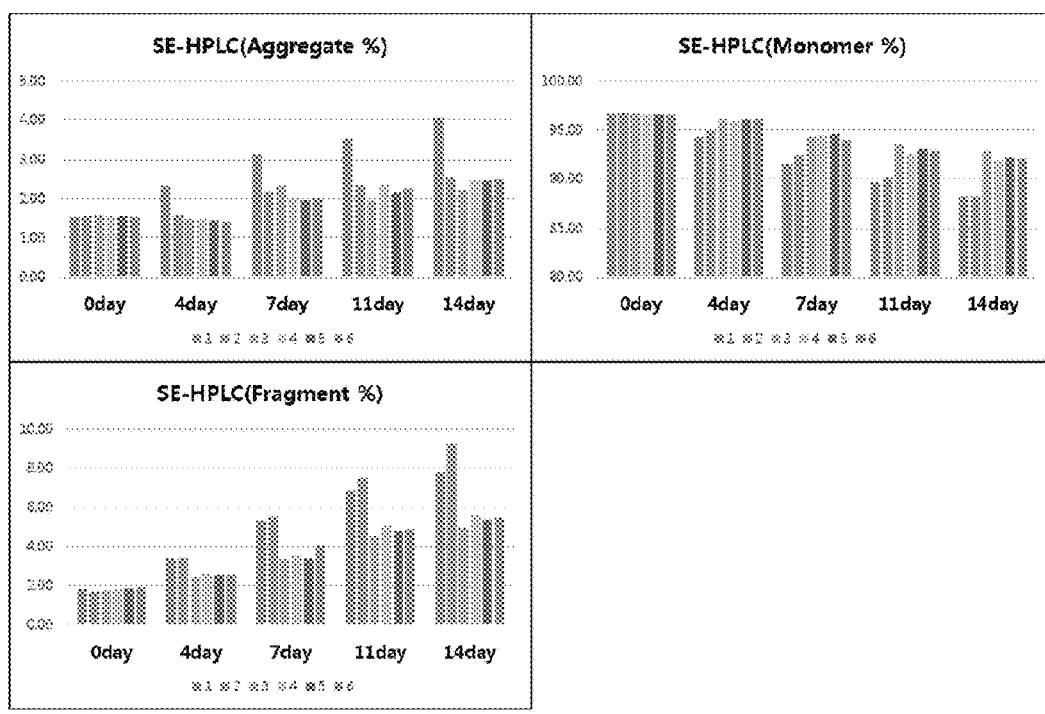
FIG. 21 illustrates results according to types of acid adjusting pH of the composition, measured by SE-HPLC.
Figure 22:
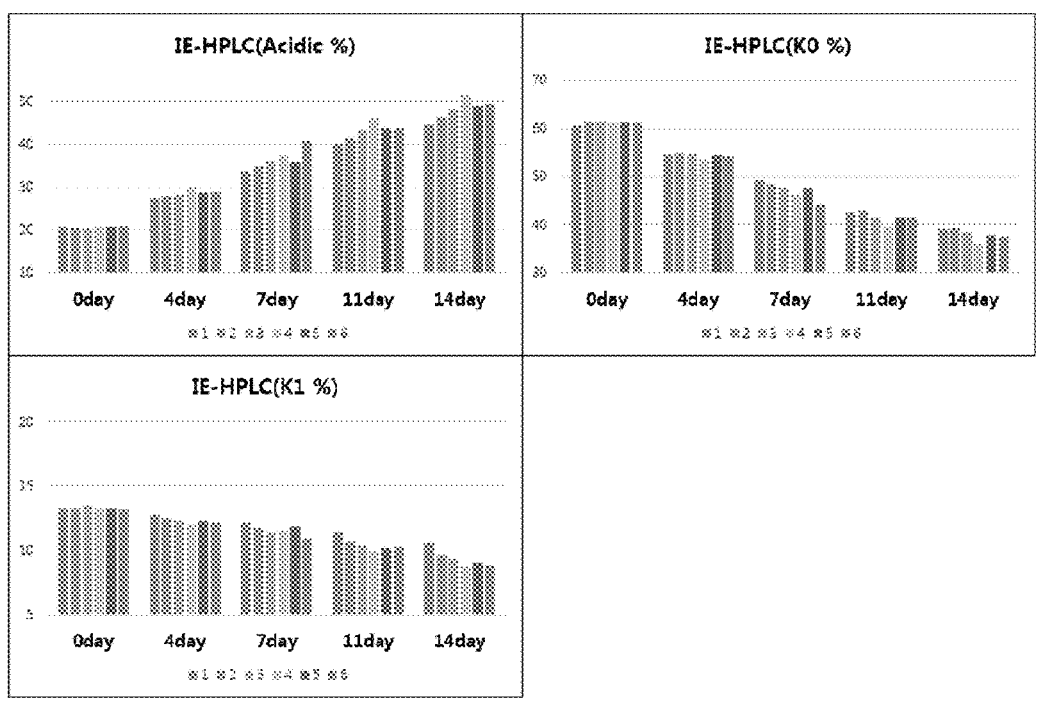
FIG. 22 illustrates results according to types of acid adjusting pH of the composition, measured by IE-HPLC.

When referring to FIG. 21, it was confirmed that only HCl containing sample shows the increase of aggregate, as compared to samples including acids adjusting pH other than HCl. Rest of samples show the similar results. it was shown that stability was better with an order of sample No. 3>sample No. 4>sample No. 5 (Citric acid>Phosphoric acid>Succinic acid). Under a condition of sample No. 3 (Citric acid) shows the most effective inhibition of aggregate. As shown in FIG. 22, however, the decrease rate of K0 is excellent with $3^{rd}$ order. When putting the results of both SEC, IE-HPLC together, it was considered that formulation including Citric acid shows the best effect.

EXAMPLE 6

The present experiment was conducted by preparing a formulation including a combination of mannitol and ammonium sulfate. In addition, citric acid was added for pH correction. Each composition was shown in Table 6.

TABLE 6

Formulation comprising combination of isotonic agents

| No. | Protein (mg/mL) | Citrate-phosphate (mM) | Citric acid (mM) | Mannitol (%) | Ammonium sulfate (mM) | Osmolality (osmol/kg) | pH |
|---|---|---|---|---|---|---|---|
| | | | 100 mM Arginine (adjust the pH to 5.9 by adding 1M citric acid) | | | | |
| 1 | 50 | 21.45 | — | 2.75 | — | 293 | 5.9 |
| 2 | 50 | — | 71.4 | 3.45 | — | 303 | |
| 3 | 50 | 21.45 | — | — | 77.5 | 293 | |
| 4 | 50 | — | 71.4 | — | 100 | 303 | |
| 5 | 50 | — | 71.4 | 2.2 | 65 | 300 | |
| 6 | 50 | — | 71.4 | 1.7 | 60 | 300 | |
| 7 | 50 | — | 71.4 | 1.2 | 46 | 295 | |

Figure 23:
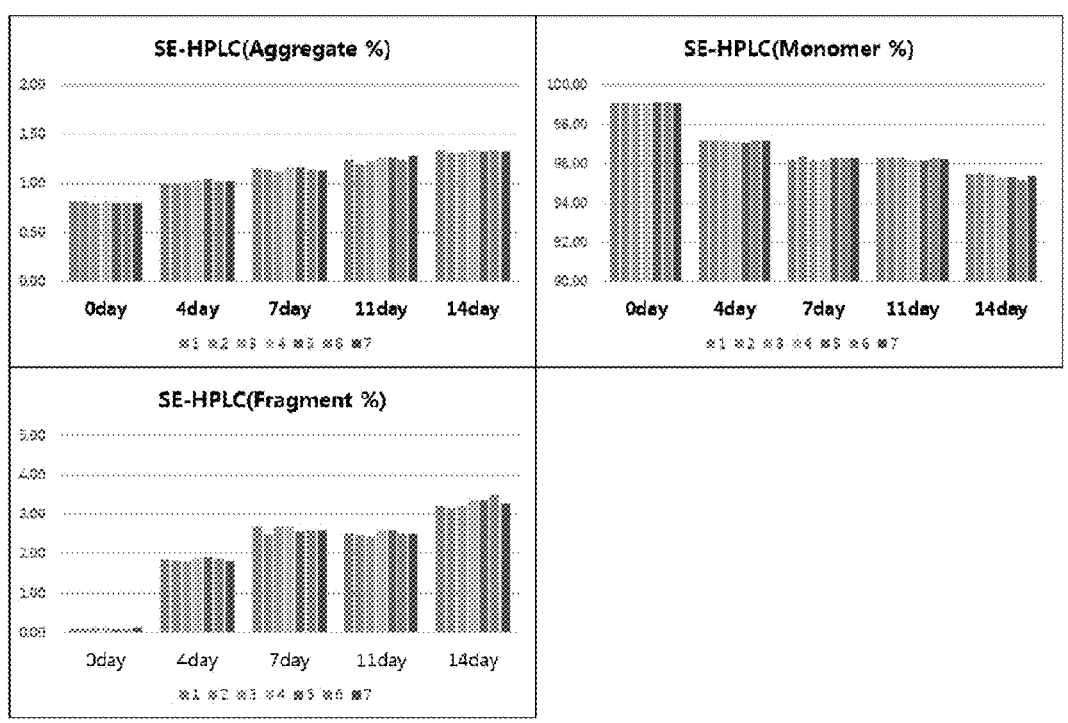
FIG. 23 illustrates results according to combinations of isotonic agents, measured by SE-HPLC.
Figure 24:
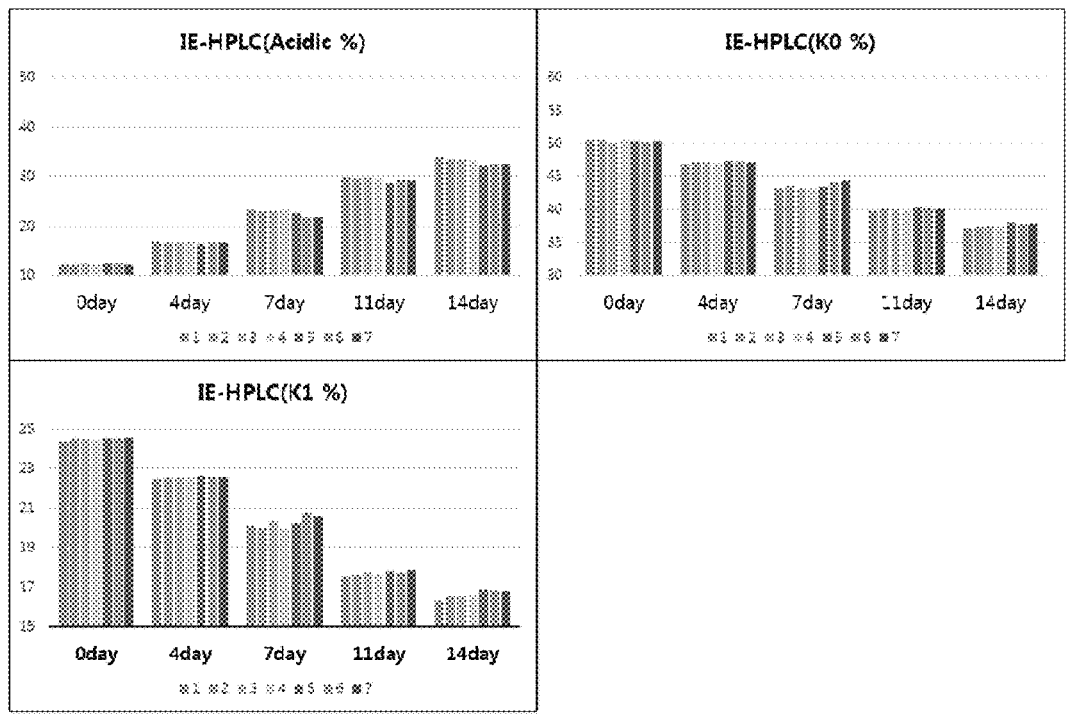
FIG. 24 illustrates results according to combinations of isotonic agents, measured by IE-HPLC.

Referring to FIG. 23, there was no significant difference in SEC and WCX results of the samples. However, referring to FIG. 24, it was confirmed that samples No. 6, and 7 had good stability against variants, and sample No. 7 had the most excellent result. As a result, it was determined that stability was excellent even in the composition including the combination of mannitol and ammonium sulfate with Citric acid buffer.

EXAMPLE 7

The present experiment is to compare a formulation developed by our own company through the above-described experiments and Humira® formulation by long-term acceleration experiments, and to confirm that the formulation developed by our own company had more excellent performance than or the same performance as the existing commercialized formulation Humira®.

Figure 25:
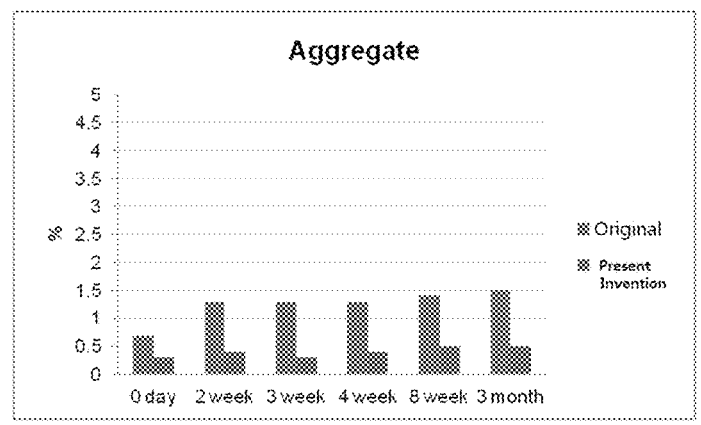
FIG. 25 illustrates results of change in aggregate content (%) between a formulation in our own company and Humira® formulation, measured for 12 weeks at 30° C.
Figure 26:
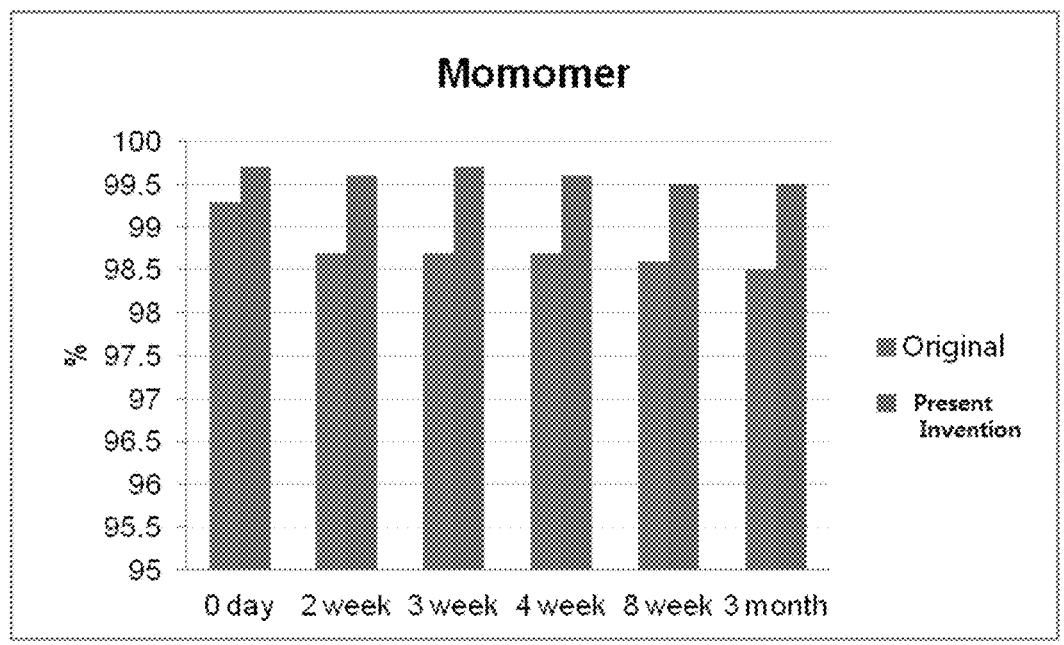
FIG. 26 illustrates results of change in monomer content (%) between the formulation in our own company and Humira® formulation, measured for 12 weeks at 30° C.
Figure 27:
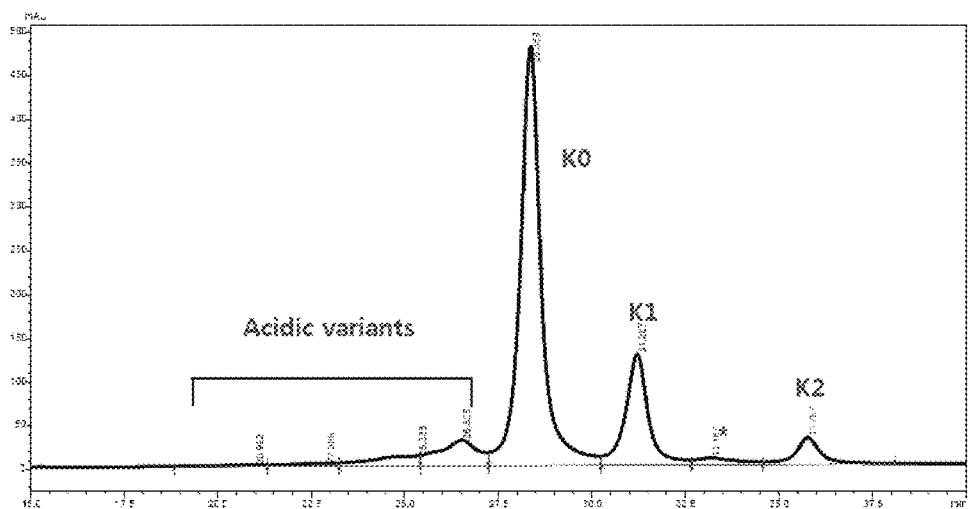
FIG. 27 illustrates results of purified adalimumab tested in high performance liquid chromatography with cation exchange (WCX: weak cation-exchange).

The stability was confirmed by storing the formulation sample developed by our own company and the Humira® formulation at 30° C., and analyzing aggregation, monomer, and fragment contents over time by SE-HPLC. The analysis was performed by TSKgel G3000SWXL (300×7.8 mm) HPLC analysis column while loading 0.2 M potassium phosphate, 0.25 M potassium chloride, pH6.2 buffer at 0.5 ml/min. From the observation results for 12 weeks at 30° C., it was confirmed that a reduction rate of monomer was low and an increase rate of aggregate and fragment was also low in the formulation developed by our own company as compared to the Humira® formulation as shown in FIGS. 25 and 26.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The composition containing basic amino acid; and sugar and/or ammonium salt used in the present invention effectively inhibits aggregation, denaturation and oxidation of TNFα-binding antibody protein, such that the protein is capable of being preserved and stored for a long time and is stabilized so as to maintain an activity for a long period of time in vivo, thereby being widely usable in a medical field using an anti-TNF-alpha antibody. In addition, even in the case in which a trace amount of surfactant is used, or surfactant is not used, the protein is capable of being stabilized.

The invention claimed is:

1. A stabilized adalimumab composition, comprising: adalimumab;
   arginine with a concentration of 50 to 100 mM;
   mannitol with a concentration of 1 to 2.5% (w/v);
   ammonium sulfate with a concentration of 40-65 mM;
   and citric acid.
2. The composition according to claim 1, pH of the composition is 5.7 to 6.3.
3. The composition according to claim 1, comprising 5 to 100 mg/ml of adalimumab.
4. The composition according to claim 1, wherein the stabilization is one selected from the following (a) to (e):
   (a) inhibition of denaturation, deamidation or oxidation of adalimumab;

(b) inhibition of reduction of K0 variants (the major peak in HPLC of lysine variants of monoclonal antibody) of C-terminal lysine;
(c) inhibition of production of acidic variants;
(d) inhibition of reduction ratio of adalimumab monomer; and
(e) inhibition of aggregation of adalimumab or inhibition of increase in production of fragments thereof.

5. A pharmaceutical formulation comprising a composition according to claim 1.

6. A method of stabilizing adalimumab comprising adding arginine, mannitol, ammonium sulfate and citric acid to a solution containing adalimumab, wherein a concentration of arginine in the solution is 50 to 100 mM, a concentration of mannitol is 1 to 2.5% (w/v) and a concentration of ammonium sulfate is 40-65 mM.

* * * * *